United States Patent
Arthur et al.

(10) Patent No.: US 9,198,684 B2
(45) Date of Patent: Dec. 1, 2015

(54) SURGICAL CUTTING DEVICE HAVING A BLUNT TIP FOR PROTECTING TISSUE ADJACENT TARGETED TISSUE AND METHOD FOR USE THEREOF

(71) Applicant: KYPHON SARL, Neuchatel (CH)

(72) Inventors: Amy L. Arthur, Mountain View, CA (US); Todd W. Jenkins, San Jose, CA (US)

(73) Assignee: KYPHON SARL, Neuchatel (CH)

( * ) Notice: Subject to any disclaimer, the term of this patent is extended or adjusted under 35 U.S.C. 154(b) by 315 days.

(21) Appl. No.: 13/838,580

(22) Filed: Mar. 15, 2013

(65) Prior Publication Data

US 2014/0276744 A1    Sep. 18, 2014

(51) Int. Cl.
*A61B 18/18* (2006.01)
*A61B 17/32* (2006.01)
*A61B 17/3205* (2006.01)
*A61B 18/14* (2006.01)
*A61B 18/00* (2006.01)

(52) U.S. Cl.
CPC ..... *A61B 17/320016* (2013.01); *A61B 17/3205* (2013.01); *A61B 17/32056* (2013.01); *A61B 18/148* (2013.01); *A61B 2017/320044* (2013.01); *A61B 2017/320064* (2013.01); *A61B 2018/00434* (2013.01); *A61B 2018/00577* (2013.01); *A61B 2018/00601* (2013.01); *A61B 2018/1412* (2013.01); *A61B 2218/007* (2013.01)

(58) Field of Classification Search
CPC ............. A61B 18/1402; A61B 18/149; A61B 18/148; A61B 17/320016; A61B 17/32056; A61B 17/3205

USPC ................................................ 606/41, 45, 39
See application file for complete search history.

(56) References Cited

U.S. PATENT DOCUMENTS

| | | |
|---|---|---|
| 5,007,908 A | 4/1991 | Rydell |
| 5,158,545 A | 10/1992 | Trudell et al. |
| 5,286,253 A | 2/1994 | Fucci |
| 5,370,651 A | 12/1994 | Summers |
| 5,540,693 A | 7/1996 | Fisher |
| 5,769,086 A | 6/1998 | Ritchart et al. |
| 5,814,058 A | 9/1998 | Carlson et al. |
| 5,891,141 A | 4/1999 | Rydell |
| 5,911,701 A * | 6/1999 | Miller et al. ................ 604/22 |
| 6,090,072 A | 7/2000 | Kratoska et al. |
| 6,932,810 B2 * | 8/2005 | Ryan ............................... 606/38 |
| 7,033,357 B2 | 4/2006 | Baxter et al. |
| 7,131,970 B2 | 11/2006 | Moses et al. |
| 7,195,631 B2 | 3/2007 | Dumbauld |
| 7,347,857 B2 | 3/2008 | Anderson et al. |
| 7,488,295 B2 | 2/2009 | Burbank et al. |
| 7,731,719 B2 * | 6/2010 | Nordt .............................. 606/79 |
| 7,967,776 B2 | 6/2011 | von Segesser |
| 8,303,586 B2 | 11/2012 | Cunningham et al. |
| 2012/0172668 A1 | 7/2012 | Kerns et al. |
| 2012/0271357 A1 | 10/2012 | Arthur et al. |
| 2013/0046304 A1 * | 2/2013 | Germain et al. ............... 606/45 |

* cited by examiner

*Primary Examiner* — Christopher D Koharski
*Assistant Examiner* — Michael Carey
(74) *Attorney, Agent, or Firm* — Sorell Lenna & Schmidt LLP

(57) ABSTRACT

A cutting device includes an elongated shaft that extends between a proximal end and a distal end. A distal arm extends from the distal end of the elongated shaft. The distal arm includes an inner surface defining a cavity and an outer surface defining a blunt tip. At least one proximal arm extends from the distal end of the elongated shaft at a position proximal to the distal arm. The at least one proximal arm has an inner surface defining a cavity including a cutting portion configured to cut tissue.

23 Claims, 3 Drawing Sheets

SURGICAL CUTTING DEVICE HAVING A BLUNT TIP FOR PROTECTING TISSUE ADJACENT TARGETED TISSUE AND METHOD FOR USE THEREOF

FIELD OF THE INVENTION

The present invention relates generally to devices and methods for cutting a material or substance. More specifically, the devices and methods are useful for resecting nerve and/or soft tissue via a minimally invasive procedure to alleviate pain.

BACKGROUND OF THE INVENTION

Standard methods of cutting tissue may include using a scalpel, scissors, and radio frequency energy. Electrosurgical procedures and techniques using radio frequency energy are currently used since they generally reduce patient bleeding and trauma associated with cutting operations. Additionally, electrosurgical ablation procedures, where tissue surfaces and volume may be reshaped, cannot be duplicated through other treatment modalities.

Minimally invasive procedures in nerve and/or soft tissue such as the spine or the breast, however, are difficult to perform using standard scissors and scalpel. Furthermore, in a closed environment, radio frequency current dissipates into the surrounding tissue causing a decreased ability to achieve a current at the cutting electrode of sufficiently high density to initiate a cut. To overcome this problem, high power settings are often required to initiate the cut which often is painful and increases thermal damage to the tissue whether using a standard or a custom electrosurgical generator.

Another problem associated with cutting tissue is the control of bleeding. Radio frequency energy controls bleeding by coagulating small blood vessels. Another method of controlling bleeding is through the use of heat. For example, some commercially available scalpels use direct heat to control bleeding. However, while the bleeding is generally controlled, the cutting of tissue is often slower than with radio frequency energy and the knife edge readily dulls. Other commercially available scalpels use ultrasonic energy generally at 50 kHz to heat the tissue so as to coagulate severed blood vessels but cut slower than a standard electrosurgical electrode and are costly as a custom ultrasonic generator is required.

A further disadvantage of using radio frequency energy is the generation of smoke. The smoke is malodorous and can contain airborne viral particles that may be infectious. Furthermore, the smoke often obscures visualization of the procedure. When the smoke becomes too dense, the procedure is delayed until the smoke is released through one of the trocar ports and after enough carbon dioxide gas has reinsufflated the abdominal cavity. This unnecessarily prolongs the operative time.

Radiofrequency (RF) energy is used in a wide range of surgical procedures because it provides efficient tissue resection and coagulation and relatively easy access to the target tissues through a portal or cannula. Conventional monopolar high frequency electrosurgical devices typically operate by creating a voltage difference between the active electrode and the target tissue, causing an electrical arc to form across the physical gap between the electrode and tissue. At the point of contact of the electric arcs with tissue, rapid tissue heating occurs due to high current density between the electrode and tissue. This high current density causes cellular fluids to rapidly vaporize into steam, thereby producing a "cutting effect" along the pathway of localized tissue heating. Thus, the tissue is parted along the pathway of evaporated cellular fluid, inducing undesirable collateral tissue damage in regions surrounding the target tissue site. This collateral tissue damage often causes indiscriminate destruction of tissue, resulting in the loss of the proper function of the tissue. In addition, the device does not remove any tissue directly, but rather depends on destroying a zone of tissue and allowing the body to eventually remove the destroyed tissue.

Present electrosurgical techniques used for tissue ablation may suffer from an inability to provide the ability for fine dissection of soft tissue. The distal end of electrosurgical devices is wide and flat, creating a relatively wide area of volumetric tissue removal and making fine dissections along tissue planes more difficult to achieve because of the lack of precision provided by the current tip geometries.

In addition, identification of the plane is more difficult because the large ablated area and overall size of the device tip obscures the physician's view of the surgical field. The inability to provide for fine dissection of soft tissue is a significant disadvantage in using electrosurgical techniques for tissue ablation, particularly in arthroscopic, otolaryngological, and spinal procedures.

Traditional monopolar RF systems can provide fine dissection capabilities of soft tissue, but may also cause a high level of collateral thermal damage. Further, these devices may suffer from an inability to control the depth of necrosis in the tissue being treated. The high heat intensity generated by these systems causes burning and charring of the surrounding tissue, leading to increased pain and slower recovery of the remaining tissue. Further, the desire for an electrosurgical device to provide for fine dissection of soft tissue may compromise the ability to provide consistent ablative cutting without significant collateral damage while allowing for concomitant hemostasis and good coagulation of the remaining tissue.

Another problem with currently available RF nerve ablation devices is that they attempt to destroy nerve tissue from a central location including the tip of the device and a 3-D spherical or cylindrical zone around it. As a result, the further away the resecting ability is from the central zone the less effective the nerve destruction. Consequently, often the nerve is not adequately ablated leading to continued pain symptoms.

Further, the health care practitioner may have difficulty positioning the tip of the device in the optimal location to get an optimal and consistent clinical result. This may also result in unwanted necrosis of adjacent tissue, which can lead to clinical adverse events including subsequent repair of the necrotic tissue.

Other devices such as mechanical ronguers can be used to remove soft tissue. However, these devices require the insertion of relatively large cannulas that further complicate the surgical procedure and can cause nerve compression and pain with variable clinical efficacy.

Accordingly, there is a need for devices and methods to provide efficient severing or cutting of nerve and/or soft tissue that can be used during a minimally invasive procedure and/or during an open surgical procedure. Further, there is also a need for devices and methods that provide fine dissection capabilities of nerve and/or soft tissue. Devices and methods that do not cause a high level of collateral thermal damage and allow for the control of necrosis in the tissue being treated are also needed. Devices and methods that provide efficient, controlled and safe debulking of tissue would also be beneficial.

SUMMARY OF THE INVENTION

This application is directed to a cutting device in accordance with the principles of this disclosure, which includes an elongated shaft that extends between a proximal end and a distal end. A distal arm extends from the distal end of the elongated shaft. The distal arm includes an inner surface defining a cavity and an outer surface defining a blunt tip. At least one proximal arm extends from the distal end of the elongated shaft at a position proximal to the distal arm. The at least one proximal arm has an inner surface defining a cavity and includes a cutting portion configured to cut tissue.

In one embodiment, a device for cutting tissue comprises an elongated shaft extending between a proximal end and a distal end. A distal arm extending from the distal end of the elongated shaft. The distal arm includes an inner surface defining a cavity and an outer surface defining a blunt tip. Two proximal arms extend from the distal end of the elongated shaft at a position proximal to the distal arm. Each of the proximal arms has an inner surface defining a cavity including a cutting portion configured to cut tissue. A vacuum attachment is disposed at the proximal end of the elongated shaft to produce suction to facilitate removal of tissue from the cavity.

In one embodiment, a method of cutting tissue comprises inserting a cannula to form a hole in the tissue. A cutting device is inserted through the cannula. The cutting device is pulled in a proximal direction by a medical practitioner such that the cutting portion cuts tissue with a single slice. The cut tissue is captured with the distal arm and directed into the cavity of the distal arm. The cutting device and the cannula are subsequently removed from the patient's anatomy as well as the cut tissue.

Additional features and advantages of various embodiments will be set forth in part in the description that follows, and in part will be apparent from the description, or may be learned by practice of various embodiments. The objectives and other advantages of various embodiments will be realized and attained by means of the elements and combinations particularly pointed out in the description and appended claims.

BRIEF DESCRIPTION OF THE DRAWINGS

In part, other aspects, features, benefits and advantages of the embodiments will be apparent with regard to the following description, appended claims and accompanying drawings where:

DETAILED DESCRIPTION OF THE INVENTION

Figure 1:
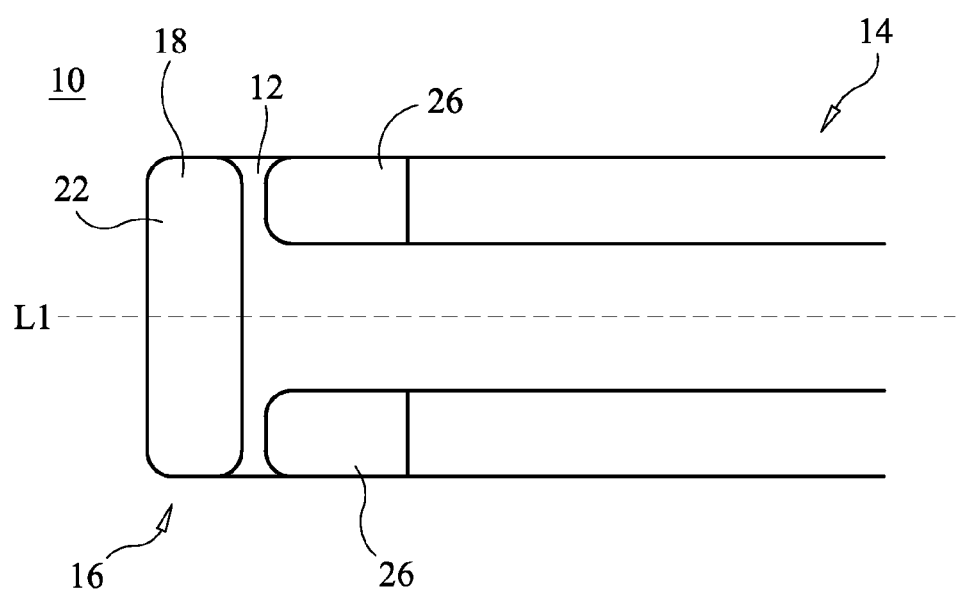
FIG. 1 is a side view of an embodiment of the device in accordance with the principles of the present disclosure.

Devices for efficient severing or cutting of a material or substance such as nerve and/or soft tissue suitable for use in open surgical and/or minimally invasive procedures are disclosed. The following description is presented to enable any person skilled in the art to make and use the present disclosure. Descriptions of specific embodiments and applications are provided only as examples and various modifications will be readily apparent to those skilled in the art.

Lumbar spinal stenosis (LSS) may occur from hypertrophied bone or ligamentum flavum, or from a lax ligamentum flavum that collapses into the spinal canal. LSS can present clinical symptoms such as leg pain and reduced function. Conventional treatments include epidural steroid injections, laminotomy, and laminectomy. Surgical interventions which remove at least some portion of the lamina are usually performed through a relatively large incision, and may result in spinal instability from removal of a large portion of the lamina. Consequently, a percutaneous approach which removes just enough tissue (lamina or ligamentum flavum) to be effective is provided.

In one embodiment, a device utilized to cut soft tissue is provided. In one embodiment, the device is positioned beyond a distal border of tissue to be cut and drawn proximally. Two razor or RF blades cut the tissue as the tool is drawn proximally. A distal finger captures and collects the cut tissue as the tool is drawn proximally to excise tissue from the area.

The present disclosure may be understood more readily by reference to the following detailed description of the disclosure presented in connection with the accompanying drawings, which together form a part of this disclosure. It is to be understood that this disclosure is not limited to the specific devices, methods, conditions or parameters described and/or shown herein, and that the terminology used herein is for the purpose of describing particular embodiments by way of example only and is not intended to be limiting of the claimed disclosure.

As used in the specification and including the appended claims, the singular forms "a," "an," and "the" include the plural, and reference to a particular numerical value includes at least that particular value, unless the context clearly dictates otherwise.

Ranges may be expressed herein as from "about" or "approximately" one particular value and/or to "about" or "approximately" another particular value. When such a range is expressed, another embodiment includes from the one particular value and/or to the other particular value.

Similarly, when values are expressed as approximations, by use of the antecedent "about," it will be understood that the particular value forms another embodiment. It is also understood that all spatial references, such as, for example, horizontal, vertical, top, upper, lower, bottom, left and right, are for illustrative purposes only and can be varied within the scope of the disclosure.

For purposes of the description contained herein, with respect to components and movement of components described herein, "forward" or "distal" (and forms thereof) means forward, toward or in the direction of the forward, distal end of the probe portion of the device that is described herein, and "rearward" or "proximal" (and forms thereof) means rearward or away from the direction of the forward, distal end of the probe portion of the device that is described herein. However, it should be understood that these uses of these terms are for purposes of reference and orientation with respect to the description and drawings herein, and are not intended to limit the scope of the claims.

Spatially relative terms such as "under", "below", "lower", "over", "upper", and the like, are used for ease of description to explain the positioning of one element relative to a second element. These terms are intended to encompass different orientations of the device in addition to different orientations than those depicted in the figures. Further, terms such as "first", "second", and the like, are also used to describe various elements, regions, sections, etc. and are also not intended to be limiting. Like terms refer to like elements throughout the description.

As used herein, the terms "having", "containing", "including", "comprising" and the like are open ended terms that indicate the presence of stated elements or features, but do not preclude additional elements or features.

For purposes of the description contained herein, "vacuum" means pressure within a space that is lower than atmospheric or ambient pressure by any amount, and although not exclusive of a condition of absolute vacuum defined by a complete absence within a space of air, fluid or other matter, the term as used herein is not meant to require or be limited to such a condition.

The headings below are not meant to limit the disclosure in any way; embodiments under any one heading may be used in conjunction with embodiments under any other heading.

Reference will now be made in detail to certain embodiments of the invention, examples of which are illustrated in the accompanying drawings. While the invention will be described in conjunction with the illustrated embodiments, it will be understood that they are not intended to limit the invention to those embodiments. On the contrary, the invention is intended to cover all alternatives, modifications, and equivalents that may be included within the invention as defined by the appended claims.

Radiofrequency (RF) ablation devices have been available to surgeons to treat many medical conditions, for example, in the treatment of tumors in lung, liver, kidney, bone and other body organs. Pulsed RF has also been used for treatment of tumors, cardiac arrhythmias, chronic and post-operative pain, bone fracture and soft tissue wounds.

The components of the cutting device can be fabricated from biologically acceptable materials suitable for medical apparatuses, including metals, synthetic polymers, ceramics, thermoplastic and polymeric material and/or their composites. For example, the components of the holding device, individually or collectively, can be fabricated from materials such as stainless steel alloys, commercially pure titanium, titanium alloys, Grade 5 titanium, super-elastic titanium alloys, cobalt-chrome alloys, stainless steel alloys, superelastic metallic alloys (e.g., Nitinol, super elasto-plastic metals, such as GUM METAL® manufactured by Toyota Material Incorporated of Japan, Fe—Mn—Si and Fe—Ni—Co—Ti composites), ceramics and composites thereof such as calcium phosphate (e.g., SKELITE™ manufactured by Biologix Inc.), thermoplastics such as polyaryletherketone (PAEK) including polyetheretherketone (PEEK), polyetherketoneketone (PEKK) and polyetherketone (PEK), carbon-PEEK composites, PEEK-BaSO4 polymeric rubbers, polyethylene terephthalate (PET), fabric, silicone, polyurethane, silicone-polyurethane copolymers based materials, polymeric rubbers, polyolefin rubbers, semi-rigid and rigid materials, thermoplastic elastomers, thermoset elastomers, elastomeric composites, rigid polymers including polyphenylene, polyamide, polyimide, polyetherimide, polyethylene, epoxy, and composites of metals and calcium-based ceramics, composites of PEEK and calcium based ceramics, and combinations of the above materials.

Various components of the cutting device may have material composites, including the above materials, to achieve various desired characteristics such as strength, rigidity, elasticity, compliance, and biomechanical performance, durability and to provide a non-stick surface. The components of the cutting device may be monolithically formed, extruded, coextruded, hot molded, cold molded, press molded, integrally connected or include fastening elements and/or coupling components, as described herein.

Figure 2:
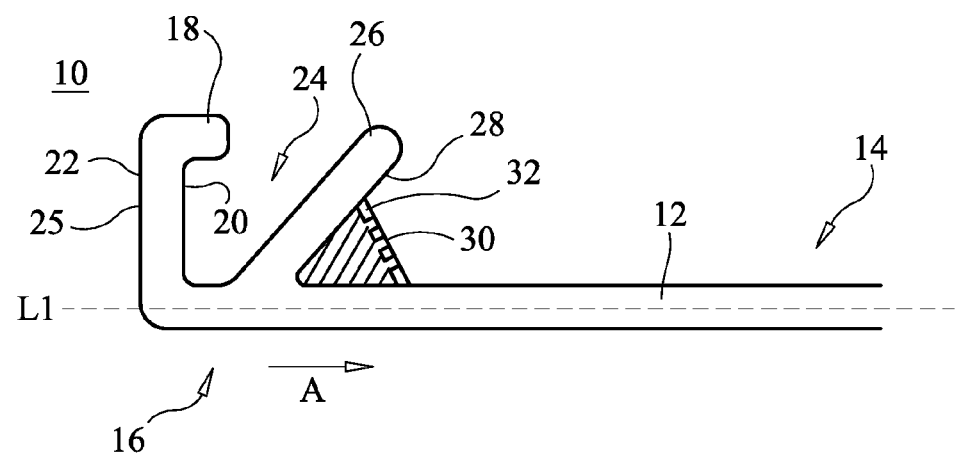
FIG. 2 is side view of components of the device shown in FIG. 1.
Figure 3:
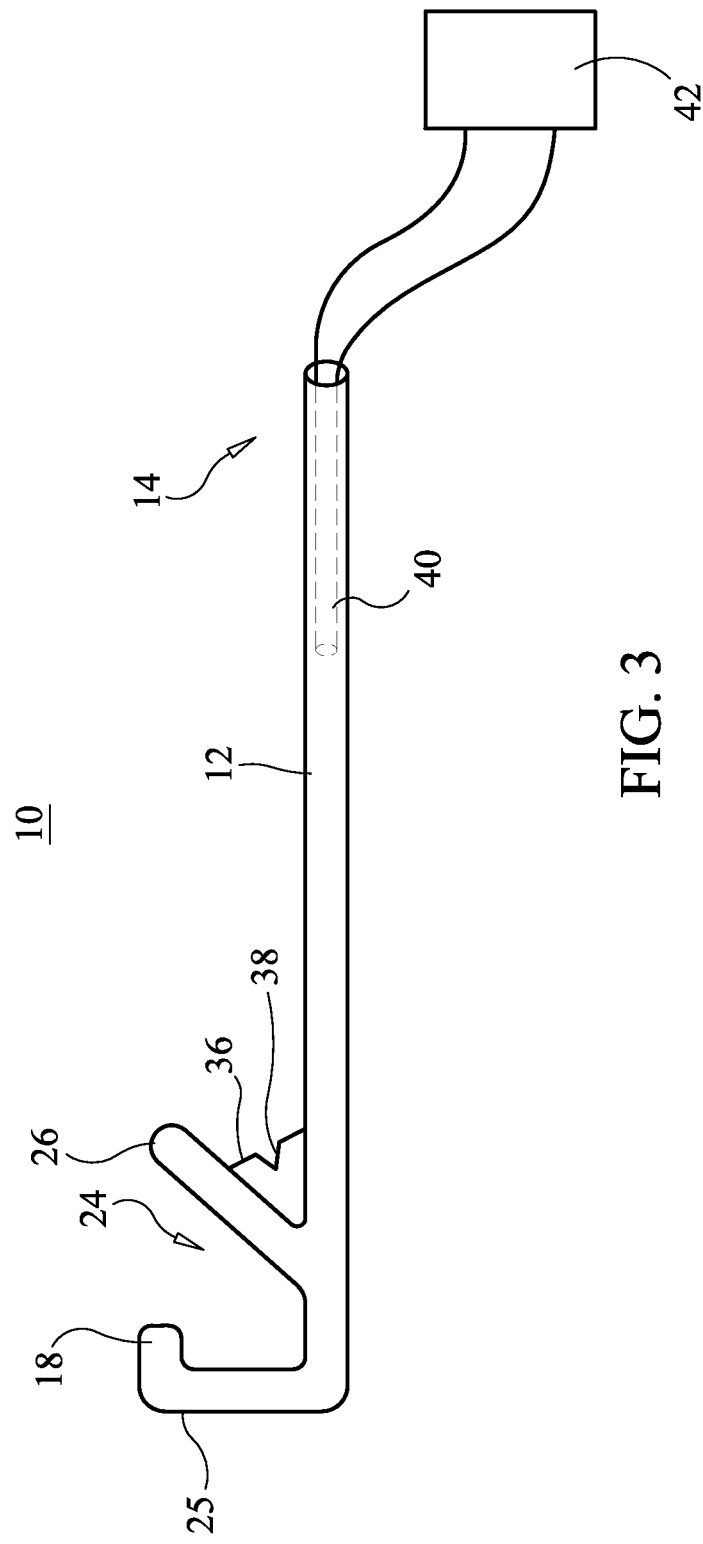
FIG. 3 is a side view of an embodiment of the device in accordance with the principles of the present disclosure.

The following discussion includes a description of a surgical device for cutting and removal of resected nerve or soft tissue and related methods of employing the device in accordance with the principles of the present disclosure. Alternate embodiments are also disclosed. Reference will now be made in detail to the exemplary embodiments of the present disclosure, which are illustrated in the accompanying figures. Turning now to FIGS. 1-3, there are illustrated components of the surgical device for cutting and removal of nerve or soft tissue in accordance with the principles of the present disclosure.

In one embodiment, the cutting device 10, in accordance with the present disclosure, includes an elongated shaft 12. Shaft 12 extends between a proximal end 14 and a distal end 16 and defines a longitudinal axis L1. It is envisioned that all or only a portion of shaft 12 may have various cross section configurations, such as, for example, cylindrical, flat, oval, oblong, triangular, square, polygonal, irregular, uniform, non-uniform, offset, staggered, undulating, arcuate, variable and/or tapered.

A distal arm 18 extends from distal end 16 of shaft 12. Arm 18 includes an inner surface 20 and an outer surface 22. Surface 20 defines a cavity 24 configured to capture tissue. In various embodiments, cavity 24 is shaped as a regular or irregular polygon including arcuate, c-shaped, round, square, oblong, kidney shaped, crescent, or beveled shape with or without ridges. Outer surface 22 defines a blunt tip 25. Tip 25 is configured to protect adjacent tissue. In some embodiments, arm 18 can be arcuate, hook and/or angled to facilitate capture of tissue. It is contemplated that surface 20 includes various surface configurations, such as, for example, smooth, rough, mesh, porous, semi-porous, dimpled and/or textured to facilitate tissue capture. In some embodiments, shaft 12 can be operatively connected to semi-steerable or navigational sources for easier guidance into tissues. In various embodiments, the navigational sources can be coupled with pre-procedure imaging means, such as, for example, CT, MRI, PET scan, etc. so that the target nerve or soft tissue to be cut can be identified and accurately located during the procedure.

Device 10 includes at least one proximal arm, such as, example, two proximal arms 26. Arms 26 extend from distal end 16 of shaft 12 at a position proximal to distal arm 16 and adjacent to each other. Arms 26 each include an inner surface 28 that defines a cutting portion 30. Cutting portion 30 is configured to contact and/or cut tissue. It is contemplated that surface 28 includes various surface configurations, such as, for example, smooth, rough, mesh, porous, semi-porous, dimpled and/or textured to facilitate tissue capture. Arms 26 are angled transverse to axis L1 of shaft 12. Cutting portions 30 are contained between arms 26 and shaft 12 such that cutting portions 30 can only cut as shaft 12 is pulled across tissue. Arms 26 extend over cutting portions 30 in an awning-like fashion such that untargeted tissue will not be cut by cutting portions 30. Arms 26 and shaft 12 prevent tissue above or below device 10 from being cut and retrieved. Arms 26 are positioned such that tissue can be cut in a single swipe by cutting portion 30.

In one embodiment, cutting portion 30 includes electrodes 32 configured to emit a RF frequency adapted for cutting nerve and/or soft tissue. In one embodiment, cutting portion 30 is configured to emit pulsed plasma signals adapted for cutting nerve and/or soft tissue. In one embodiment, device 10 includes an electrically insulated layer adjacent to and exposing cutting portion 30 such that the energy transmitted from the RF frequency and/or the plasma is centralized at cutting portion 30. In some embodiments, the coating or insulating layer can be glass or ceramic having a thickness from about 0.005 to about 0.5 mm thick or from about 0.01 to about 0.2 mm thick. By moving shaft 12 across tissue the RF or plasma signals will cut the tissue.

In one embodiment, as shown in FIG. 3, cutting portion 30 includes a blade 36. In one embodiment, blade 36 includes a recess 38 configured to ensnare and/or capture tissue for cutting. Recess 38 is configured to aid in the capture of resected tissue in addition. In one embodiment, recess 38 is configured to contain additional cutting means, such as, for example, plasma cutters or RF electrodes. Further, recess 38 is configured to stabilize the cut across a plane of tissue, such as, for example, the ligamentum flavum. As device 10 is pulled across tissue, recess 38 serves as a guide keeping the tissue to be cut in line with the cutting portion. In one embodiment blade 36 does not have recess 38.

In one embodiment, shaft 12 includes an internal passage 40 configured to engage a vacuum 42, as shown in FIG. 3, to remove the resected nerve and/or soft tissue via suction. Internal passage 40 may extend partially through shaft 12, or may extend through shaft 12 to cutting portion 30. Alternatively, an additional channel is possible for delivering fluid to the surgical site. At its proximal end, shaft 12 can be operatively connected to vacuum 42 for providing suction to resected nerve and/or tissue. Vacuum 42 may be used to transmit vacuum from a vacuum source (not shown) to a receiving aperture connected to shaft 12. Any suitable aspirator, cylindrical or otherwise, or other mechanism that creates vacuum upon the movement of an actuating member thereof, may be utilized as a vacuum source, such as, for example, a syringe or a mechanical vacuum. In one embodiment, vacuum 42 is in communication with cavity 24 for providing suction to remove cut nerve and/or soft tissue.

The present disclosure also provides methods for cutting or resectioning nerve and/or soft tissue. The methods comprise positioning a distal region of shaft 12 of cutting device 10 adjacent a nerve or soft tissue to be cut. Tip 25 of distal end 16 is blunt so as not to pierce certain areas of the patient, such as, for example, the spinal cord. Distal end 16 is positioned at the area where the tissue is to be cut. To cut the tissue, shaft 12 is pulled in the proximal direction, shown by arrow A, such that cutting portion 30 slices the tissue as it is being pulled. As device 10 moves proximally, cavity 24 is moved over the nerve and/or soft cut tissue and arm 18 captures the cut tissue and directs the cut tissue into cavity 24. Vacuum 42 can be utilized to remove the cut nerve and/or soft tissue such that device 10 can be reinserted for additional cutting.

In another embodiment, the cutting device defines a small channel configured for injection of irrigation fluid to the surgical site to wash out the surgical site, facilitate suction of loose tissue fragments, and/or to cool the tissue.

In one embodiment, shaft 12 is operatively coupled to a source of navigational capability to allow easier pushing through the tissues. In various embodiments, the methods of cutting disclosed herein can include a pre-procedure step wherein the probe or needle can be coupled to a CT, MRI, PET machine, or the like so that the target nerve and/or soft tissue to be cut can be identified and accurately located during the resection procedure.

The methods for cutting described hereinabove allow complete resection of the nerve avoiding the problems and partial effectiveness of current RF and cryoablation devices available in the art, and also allow for easier, more efficient, more complete, and safer removal of soft tissue that is causing stenosis pain symptoms.

It will be apparent to those skilled in the art that various modifications and variations can be made to various embodiments described herein without departing from the spirit or scope of the teachings herein. Thus, it is intended that various embodiments cover other modifications and variations of various embodiments within the scope of the present teachings.

What is claimed is:

1. A cutting device for cutting targeted tissue, the cutting device comprising:
    an elongated shaft extending between a proximal end and a distal end, the elongated shaft defining a longitudinal axis;
    a first arm extending from the distal end of the elongated shaft substantially perpendicular to the longitudinal axis, the first arm including an inner surface defining a first cavity between the inner surface and the elongated shaft, and an outer surface defining a blunt tip, the blunt tip defining a first protective portion, the first protective portion being configured to protect at least a first portion of tissue, adjacent to the targeted tissue from being cut;
    at least one second arm, the at least one second arm having a first end contacting the elongated shaft at a position intermediate the proximal end of the elongated shaft and the distal end of the elongated shaft, a second end spaced away from the elongated shaft, a length between the first end and the second end, the length defining a substantially straight line, the line having a plurality of points defined thereon between the first end and the second end, and an inner surface defining a second cavity; and
    a cutting portion configured to cut tissue, the cutting portion extending from a first position in contact with the elongated shaft to a second position in contact with the at least one second arm, the second position being intermediate the first end of the at least one second arm and the second end of the at least one second arm, defining an overhanging portion of he at least one second arm extending from the second position of the cutting portion to the second end of the at least one second arm;
    wherein each point on the line defined by the length of the second arm defines a substantially acute angle with respect to the longitudinal axis; and
    wherein the overhanging portion of the at least one second arm defines a second protective portion, the second protective portion being configured to protect at least a second portion of tissue, adjacent to the targeted tissue, from being cut.

2. A cutting device as recited in claim 1, wherein the at least one second arm includes at least two arms extending adjacent to each other from the elongated shaft at the position.

3. A cutting device as recited in claim 1, wherein the first arm includes an arcuate shape configured to capture and collect cut targeted tissue and direct the cut targeted tissue into at least one of the first cavity and the second cavity.

4. A cutting device as recited in claim 1, wherein the at least one second arm defines at least one second cavity between the at east one second arm and the elongated shaft.

5. A cutting device as recited in claim 1, wherein the cutting portion includes electrodes configured to emit a radio frequency energy, the radio frequency energy being adapted to cut the targeted tissue.

6. A cutting device as recited in claim 1, wherein the cutting portion is configured to emit plasma energy, the plasma energy being adapted for destruction of the targeted tissue.

7. A cutting device as recited in claim 1, wherein the elongated shaft further includes an attachment to a vacuum so as to produce suction to remove cut targeted tissue from at least the first cavity.

8. A cutting device as recited in claim 5, wherein the device includes an electrically insulated layer adjacent to and exposing the cutting portion, thereby centralizing the radio frequency energy.

9. A cutting device as recited in claim 1, wherein the cutting portion includes at least one blade.

10. A cutting device as recited in claim 9, wherein the at least one blade includes a notch, the notch being configured to at least one of ensnare and capture the targeted tissue.

11. A device for cutting targeted tissue, the device comprising:
an elongated shaft extending between a proximal end and a distal end, the elongated shaft defining a longitudinal axis;
a first arm extending from the distal end of the elongated shaft substantially perpendicular to the longitudinal axis, the first arm including an inner surface defining a first cavity between the inner surface and the elongated shaft, and an outer surface defining a blunt tip, the blunt tip defining a first protective portion, the first protective portion being configured to protect at least a first portion of tissue adjacent to the targeted tissue from being cut;
two second arms, at least one second arm of the two second arms having a first end contacting the elongated shaft at a position intermediate the proximal end of the elongated shaft and the distal end of the elongated shaft, a second end spaced away from the elongated shaft, a length between the first end and the second end, the length defining a substantially straight line between the first end and the second end, the line having a plurality of points defined thereon between the first end and the second end, and an inner surface defining a second cavity;
at least one cutting portion, the at least one cutting portion being configured to cut tissue, and extending from a first position in contact with the elongated shaft to a second position in contact with the at least one second arm, the second position being intermediate the first end of the at least one second arm and the second end of the at least one second arm, defining an overhanging portion of the at least one second arm extending from the second portion of the cutting portion to the second end of the at least one second arm; and
an attachment to a vacuum disposed at the proximal end of the elongated shaft to produce suction so as to remove tissue from at least one of the first cavity and the second cavity;
wherein each point on the line defined by the length of the second arm defines a substantially acute angle with respect to the longitudinal axis; and
wherein the overhanging portion of the at least one second arm defines a second protective portion, the second protective portion being configured to protect at least a second portion of issue adjacent to the targeted tissue, from being cut.

12. A cutting device as recited in claim 11, wherein the first arm includes a hook shape configured to capture and collect cut targeted tissue and direct the cut targeted tissue into at least one of the first cavity and the second cavity.

13. A cutting device as recited in claim 11, wherein the cutting portion is a blade.

14. A cutting device as recited in claim 11, wherein the cutting portion includes electrodes configured to emit a radio frequency energy, the radio frequency energy being adapted to cut the targeted tissue.

15. A cutting device as recited in claim 11, wherein the cutting portion is configured to emit a plasma energy, the plasma energy being adapted for destruction of the targeted tissue.

16. A cutting device as recited in claim 14, wherein the device includes an electrically insulated layer adjacent to and exposing the cutting portion thereby centralizing the radio frequency energy.

17. A cutting device as recited in claim 16, wherein the the radio frequency energy is centralized in at least one of the first cavity and the second cavity.

18. A method of cutting targeted tissue in a patient, the method comprising:
inserting a cannula in the patient, proximate the targeted tissue;
utilizing a cutting device, the cutting device comprising:
an elongated shaft extending between a proximal end and a distal end, the elongated shaft defining a longitudinal axis;
a first arm extending from the distal end of the elongated shaft substantially perpendicular to the longitudinal axis, the first arm including an inner surface defining a first cavity between the inner surface and the elongated shaft, and an outer surface defining a blunt tip, the blunt tip defining a first protective portion, the first protective portion being configured to protect tissue adjacent to the targeted tissue from being cut;
two second arms, at least one second arm of the two second arms having a first end contacting the elongated shaft at a position intermediate the proximal end of the elongated shaft and the distal end of the elongated shaft, a second end spaced away from the longitudinal shaft, a length between the first end and the second end, the length defining a substantially straight line between the first end and the second end, the line having a plurality of points defined thereon between the first end and the second end, and an inner surface defining a second cavity;
at least one cutting portion, the at least one cutting portion being configured to cut tissue, and extending from a first position in contact with the elongated shaft to a second position in contact with at the at least one second arm the second position being intermediate the first end of the at least one second arm and the second end of the at least one second arm, defining an overhanging portion extending from the second position of the cutting portion to the second end of the at least one second arm; and
an attachment to a vacuum disposed at the proximal end of the elongated shaft to produce suction to remove tissue from the cavity;
wherein each point on the line defined by the length of the second arm defines a substantially acute an angle with respect to the longitudinal axis; and
wherein the overhanging portion of the at least one second arm defines a second protective portion, the second protective portion being configured to protect at least a second portion of tissue, adjacent the targeted tissue, from being cut;
inserting the cutting device through the cannula;
pushing aside at least the first portion of tissue, adjacent to the targeted tissue, with the first protective portion;
pushing aside at least the second portion of tissue, adjacent to the targeted tissue, with the second protective portion;
pulling the cutting device in a proximal direction such that the cutting portion cuts the targeted tissue, thereby defining cut targeted tissue;
capturing the cut targeted tissue with at least the first arm and directing at least a portion of the cut targeted tissue into the second cavity; and
removing the cutting device and the cannula.

19. A method of cutting tissue as recited in claim 18, further comprising suctioning the cut targeted tissue from at least one of the first cavity and the second cavity.

20. A device as recited in claim 13, wherein the blade includes a notch, the notch being configured to at least one of ensnare and capture the targeted tissue.

21. A method as recited in claim 18, wherein the cutting device includes a cutting blade.

22. A method as recited in claim 18, wherein the cutting device includes an RF energy transmitter.

23. A method as recited in claim 18, wherein the cutting device includes a plasma energy transmitter.

* * * * *